(12) United States Patent
Cuthbert

(10) Patent No.: US 6,736,335 B2
(45) Date of Patent: May 18, 2004

(54) SCENT DISPENSING PACKET (76) Inventor: Lee Clayton Cuthbert, 2 Townsend St. #2-608, San Francisco, CA (US) 94107

(*) Notice: Subject to any disclaimer, the term of this patent is extended or adjusted under 35 U.S.C. 154(b) by 137 days.

(21) Appl. No.: 10/185,548

(22) Filed: Jun. 28, 2002

(65) Prior Publication Data

US 2004/0000599 A1 Jan. 1, 2004

Related U.S. Application Data (60) Provisional application No. 60/302,742, filed on Jul. 3, 2001.

(51) Int. Cl.$^7$ ................................................. B65D 1/32
(52) U.S. Cl. .................... 239/327; 239/326; 239/53; 239/57; 428/905
(58) Field of Search ...................... 239/34, 51.5, 53, 239/54, 55, 56, 57, 326, 327, 328, 42; 428/905, 307; 206/484

(56) References Cited

U.S. PATENT DOCUMENTS

| | | | | |
|---|---|---|---|---|
| 630,277 A | * | 8/1899 | Weitling | 239/327 |
| 1,490,496 A | * | 4/1924 | Trevillian | 222/209 |
| 2,699,888 A | * | 1/1955 | Crane | 222/212 |
| 4,161,284 A | * | 7/1979 | Rattan | 239/43 |
| 4,278,206 A | * | 7/1981 | Prussin | 239/327 |
| 4,283,011 A | * | 8/1981 | Spector | 239/36 |
| 4,306,679 A | * | 12/1981 | Dusek et al. | 239/59 |
| 4,306,892 A | * | 12/1981 | Atalla et al. | 96/222 |
| 4,387,849 A | * | 6/1983 | Van Loveren et al. | 239/6 |
| 4,484,768 A | * | 11/1984 | Norfleet | 283/116 |
| 4,817,860 A | * | 4/1989 | Shapiro | 229/80 |
| 4,854,501 A | * | 8/1989 | Ricci | 239/54 |
| 4,858,831 A | * | 8/1989 | Spector | 239/326 |
| 5,188,236 A | * | 2/1993 | Sayers et al. | 206/581 |
| 5,242,111 A | * | 9/1993 | Nakoneczny et al. | 239/47 |
| 5,364,027 A | * | 11/1994 | Kuhn | 239/44 |
| 5,391,420 A | * | 2/1995 | Bootman et al. | 428/195 |
| 5,419,958 A | * | 5/1995 | Charbonneau | 428/315.5 |
| 5,503,332 A | * | 4/1996 | Glenn | 239/56 |
| 5,535,885 A | * | 7/1996 | Daniel et al. | 206/484 |
| 6,123,221 A | * | 9/2000 | Simpson | 221/33 |
| 6,460,781 B1 | * | 10/2002 | Garcia et al. | 239/327 |

FOREIGN PATENT DOCUMENTS

WO    WO 99/59881    * 11/1999    ............ B65D/1/32

* cited by examiner

Primary Examiner—Gregory L. Huson
Assistant Examiner—Amanda Flynn
(74) Attorney, Agent, or Firm—William L. Paradice, III (57) ABSTRACT A small, substantially flat, envelope-shaped scent dispensing packet contains a porous, absorbent scent emitting material which retains a desired scent or fragrance. Compressing the packet forces scent-laden air within the packet through an opening in the packet, thereby delivering the scent to a user.

2 Claims, 8 Drawing Sheets

FIG. 1

FRONT PAGE VIEW

FIG. 2

SCENT DISPENSING PACKET

SCENT DISPENSING PACKET

This invention claims the benefit of the prior filing of my provisional patent No. 60/302742 with the US Patent Office on Jul. 3, 2001.

FEDERALLY SPONSORED RESEARCH

Not Applicable

SEQUENCE LISTING OR PROGRAM

Not Applicable

BACKGROUND—FIELD OF INVENTION

This invention relates to scent dispensing packets, specifically to scent dispensing packets that can be distributed manually, through vending machines or through the mail.

BACKGROUND—PRIOR ART

It has become common practice to distribute fragrance samples to potential customers by inserting scent strips in magazines or mailings. The scent strip process involves microencapsulating a fragrance and adhering it with glue to a printed magazine or mailing insert. The fragrance is released when the microcapsules are burst. This is usually accomplished by separating two sheets containing the microcapsules that have been temporarily adhered to one another. These burst microcapsules emit a scent because they are exposed to the air. This limits the reuse of this system as a sampling vehicle because the fragrance material cannot be easily protected from evaporation. Fragrance material is very volatile and evaporates quickly.

For instance, U.S. Pat. Nos. 5,188,236 (Sayers. et al.), 5,391,420 (Bootman, et al.), and 4,817,860 (Shapiro) all disclose releasing fragrance samples through bursting microcapsules adhered to a substrate paper or cardboard backing. U.S. Pat. No. 5,419,958 (Charbonneau) discloses a process for preventing unwanted escape of fragrance material prior to fracturing of the microcapsules. However, in all of this prior art, the problem of quick evaporation of the fragrance material once the microcapsules are burst still exists.

This problem also exists with U.S. Pat. No. 6,123,221 (Simpson) which discloses a process to deliver folded scented coupons in a dispenser. These coupons contain microcapsules that fracture as the coupons are removed from the dispenser. Once the coupons have been activated, the scent quickly evaporates.

It has become standard practice in the cosmetics industry to mail or otherwise distribute samples of fragrances to potential customers. Frequently such samples are distributed in the form of "vial-on-cards", which usually comprise a glass or plastic vial fastened to a cardboard backing. Another known means for packaging a unit dosage cosmetic sample or fragrance is the soft gelatin capsule. Similar in function to plastic or glass vials, these "soft gel" capsules contain a fluid sample of the fragrance.

These types of fragrance samples are awkward to use because they are so small. The fragrance must be applied to the skin to experience its intended scent because it is otherwise too concentrated. Once a fragrance is applied to the skin it begins to evaporate and can wear off in a matter of hours. U.S. Pat. No. 5,535,885 (Daniel, et al.) discloses a means to produce a unit-dose container that can survive the rigors of shipment through the mail or inclusion in printed material but it still does not solve the inherent problem of ease of use and reduction of evaporation once the fragrance has been released from the container. Devices that do not expose volatile fragrance oils or burst microcapsules directly to the surrounding air can diminish the rate of scent evaporation. This is accomplished by enclosing scented elements in a sack or "sachet". The purpose of these sacks is to slowly deliver a pleasant scent to an area, usually to mask an unpleasant odor. U.S. Pat. Nos. 5,503,332 (Glenn), 4,306,892 (Atalie, et al.), and 4,854,501 (Ricci) all disclose fragrance holders for scenting the surrounding area by permeation of scents into the air. These sacks are not effective promotion vehicles for delivering scent samples because they are not convenient to distribute through the mail due to their size and shape. In addition, they have the disadvantage of delivering scent to a wide area thereby causing the scent to linger for an extended period of time.

OBJECTS AND ADVANTAGES

Accordingly, several objects and advantages of my invention are:

(a) to provide a scent dispensing packet which minimizes evaporation of the scented material:

(b) to provide a scent dispensing packet which is easy to activate:

(c) to provide a scent dispensing packet which is small, lightweight and portable:

(d) to provide a scent dispensing packet which is reusable:

(e) to provide a scent dispensing packet which provides a true fragrance experience without having to apply the fragrance to the skin:

(f) to provide a scent dispensing packet which delivers a "personal" scent experience to the user without delivering scent to the surrounding area:

(g) to provide a scent dispensing packet which can be easily affixed to paper, cardboard or other material for promotional use:

(h) to provide a scent dispensing packet which can be cost effectively sent through the mail and:

(i) to provide a scent dispensing packet onto which graphics can be printed.

Further objects and advantages of my invention will become apparent from a consideration of the drawings and ensuing description.

SUMMARY

In accordance with the present invention, a packet which dispenses a sample of scent laden air when the user squeezes the sides of the packet is disclosed. For some embodiments, the scent dispensing packet is substantially flat and adapted to be provided within a greeting card.

DRAWINGS

Drawing Figures

Reference Numerals in Drawings 10 packet side or wall
14 airflow valve opening
16 airflow valve
18 design element for thumb placement
20 scent emitting material holder
22 scent emitting material
26 air surrounding scent emitting material
28 direction of airflow out of packet
30 direction of airflow into packet
32 bottom of packet
34 top of packet
36 interlocking grooves
38 direction to fold bottom and top of packet during assembly
40 flexible hinge between bottom and top of packet
42 location on packet for attaching purchase incentive
44 purchase incentive
46 inside of greeting card onto which packet can be affixed
48 advertising or promotion card onto which packet can be affixed
50 marketing copy promoting fragrance or aroma printed on card
52 marketing copy promoting fragrance or aroma printed on packet DETAILED DESCRIPTION AND OPERATION
Preferred Embodiments—FIGS. 1–6

Figure 1:
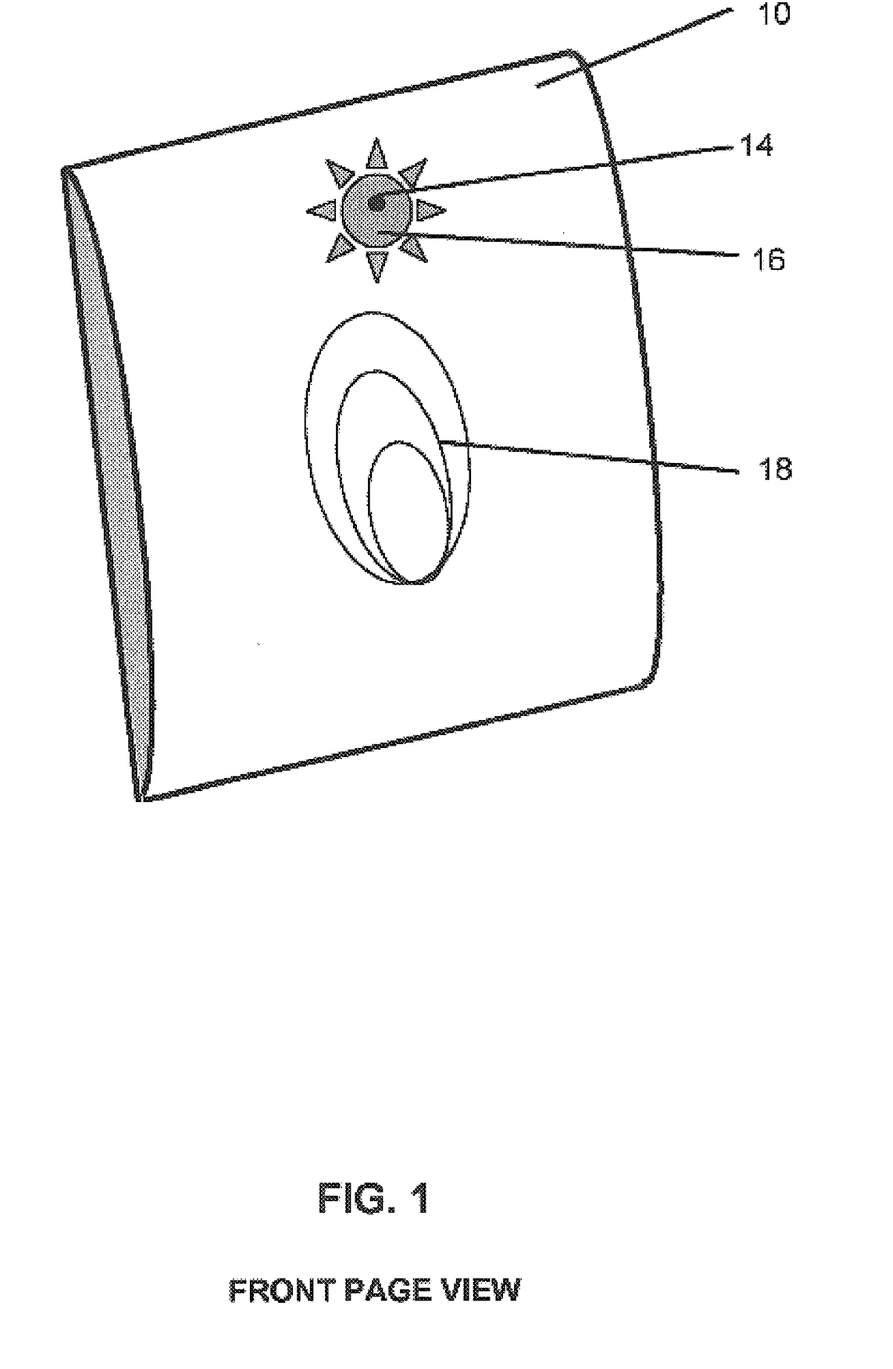
FIG. 1 is a perspective front view of a scent dispensing packet at an equalized air pressure state.
Figure 2:
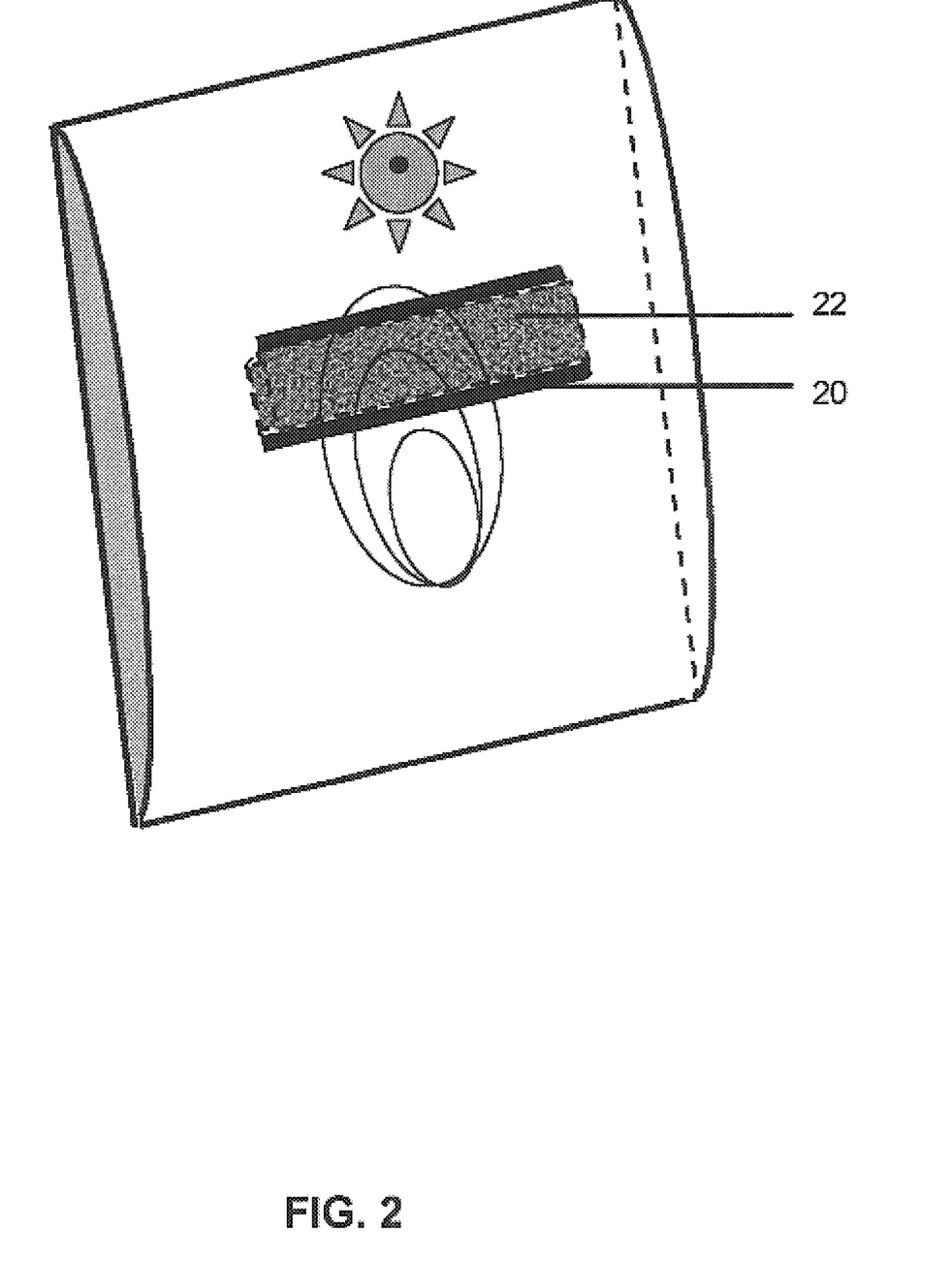
FIG. 2 is a perspective front view of the scent dispensing packet of FIG. 1 showing how a scent emitting material is housed in the scent dispensing packet.
Figure 3:
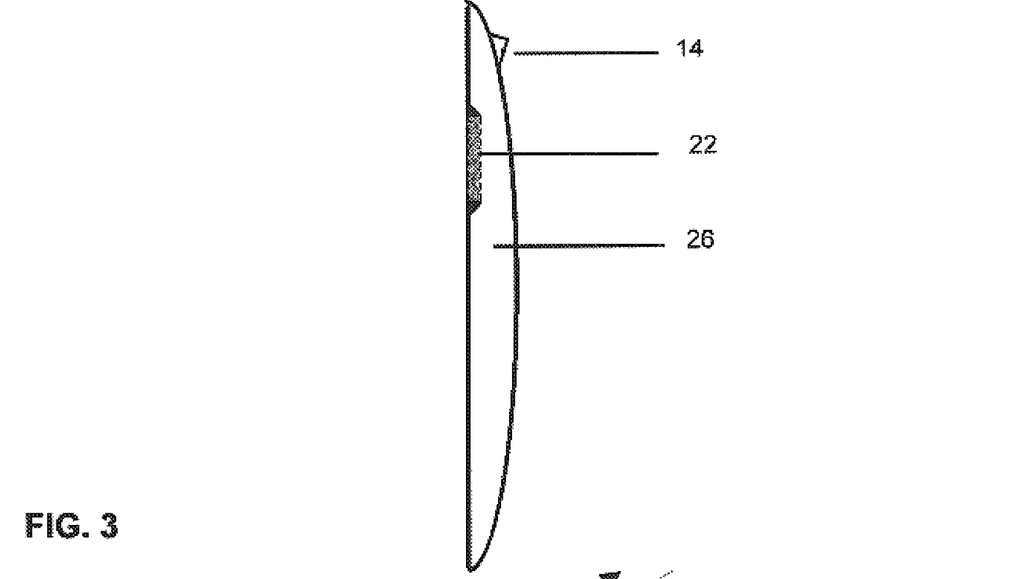
FIG. 3 is a side view of the scent dispensing packet of FIG. 1 at an equalized air pressure state.
Figure 4:
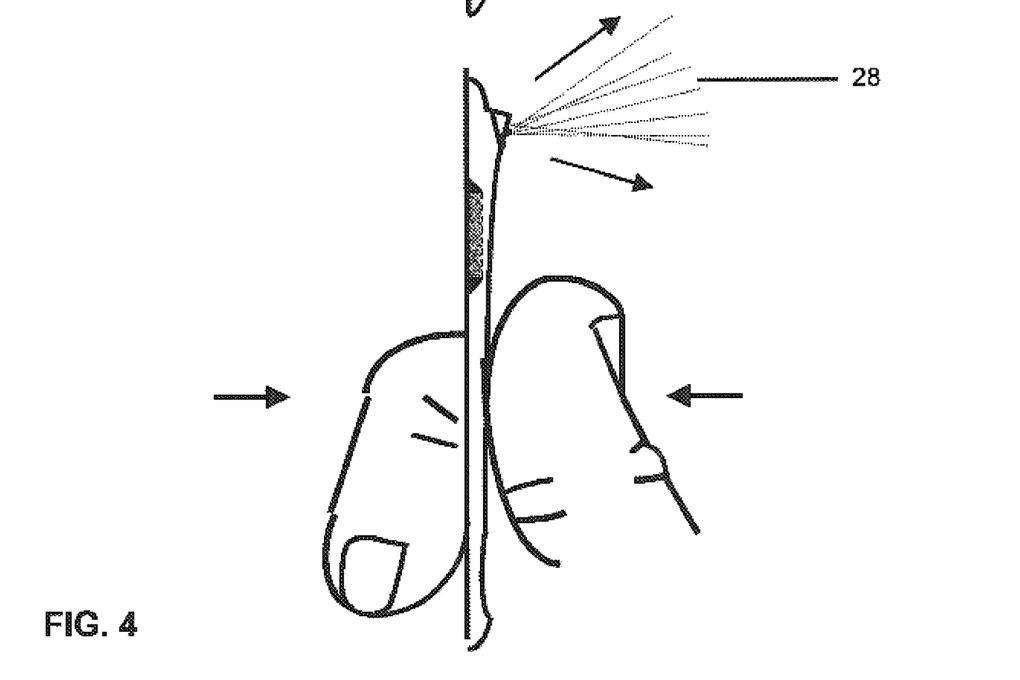
FIG. 4 is a side view of the scent dispensing packet of FIG. 1 showing how the scent dispensing packet dispenses scent as it is activated or squeezed.
Figure 5:
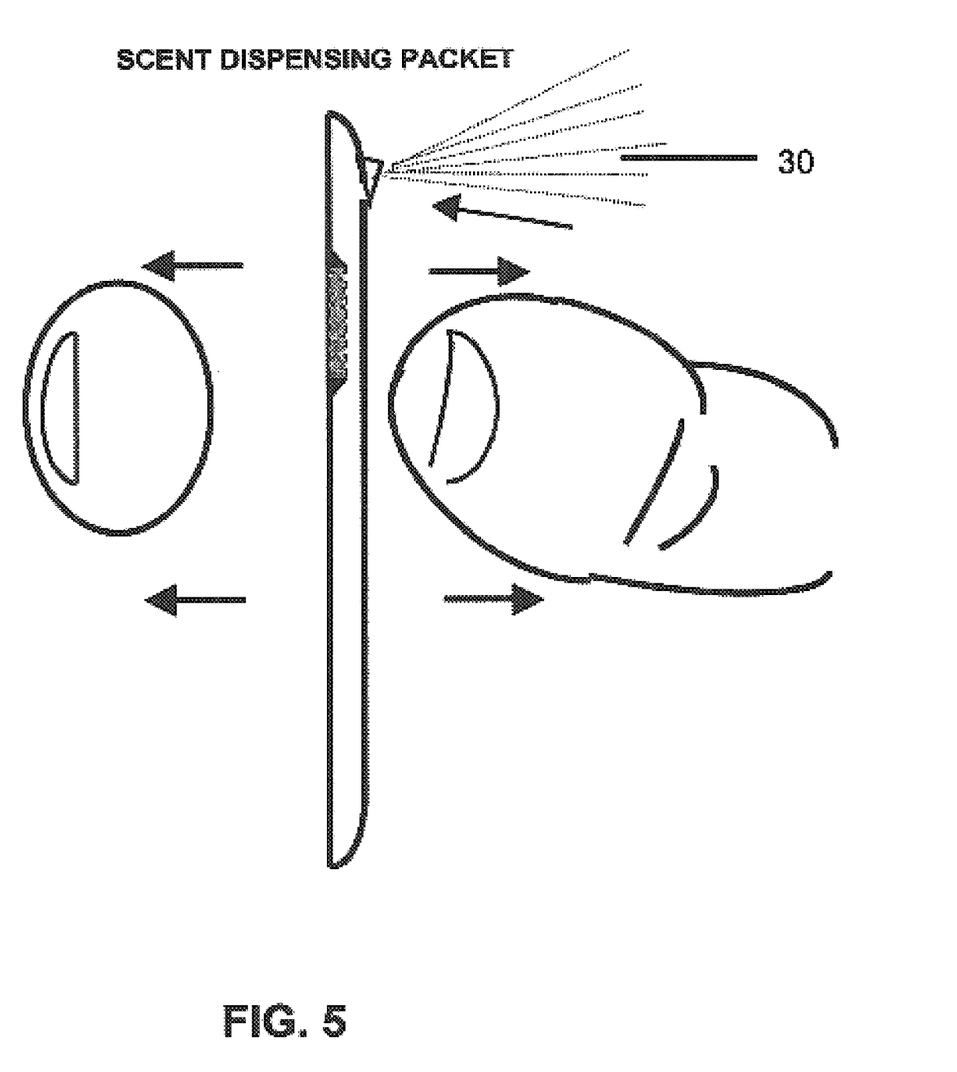
FIG. 5 is a side view of the scent dispensing packet of FIG. 1 showing the packet as it returns to an equalized air pressure state.
Figure 6:
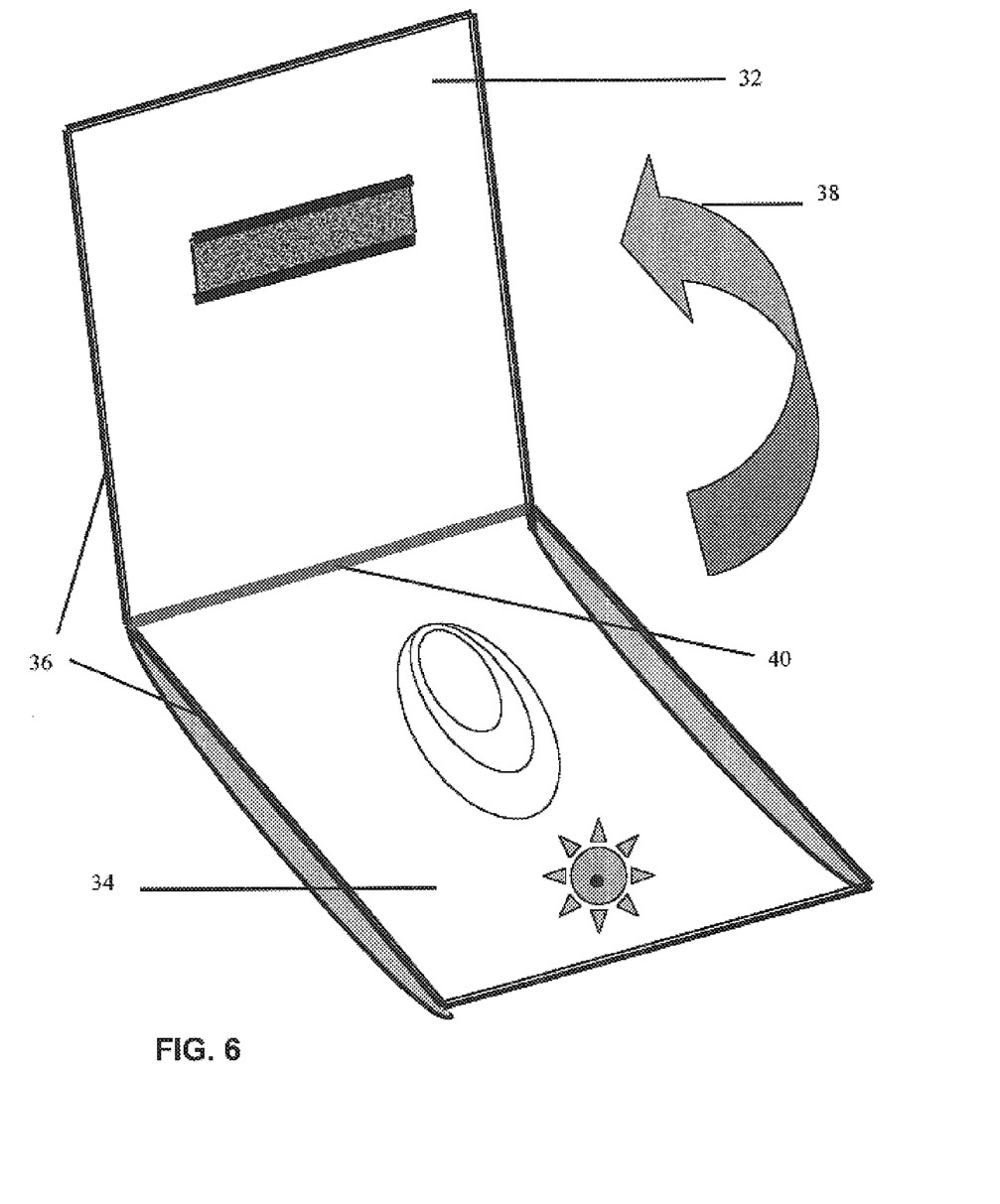
FIG. 6 is a perspective front view of the scent dispensing packet prior to assembly

A preferred embodiment of the invention is illustrated in FIGS. 1, 2, and 6 (perspective front view) and FIGS. 3, 4, and 5 (side view). FIG. 1 is a perspective view taken from the viewer's front of a scent dispensing device or scent dispensing packet constructed in accordance with the invention. The packet side or outer wall is made of plastic, foil or foil laminate or any other impermeable, flexible, thin material that can be sealed or molded in the shape of the packet. When the packet is activated or squeezed, air escapes through an airflow valve opening 14 in the center of an airflow valve 16. The valve or opening can be made of plastic or any other durable, moldable material. It can be part of the molded packet design. It allows air to pass into and out of the space inside the packet. A design element 18 can be included as part of the scent dispensing packet mold to indicate to the user where to put his/her thumb on the packet for activation or squeezing. FIG. 2 is a perspective front view of the scent dispensing packet showing the location of a scent emitting material holder 20. The holder can be molded into the side or wall of the scent dispensing packet material. It acts to hold a scent emitting material 22 in place inside the packet. The scent emitting material contained within the packet is made of a porous material that will absorb a scent or fragrance. This scent or fragrance can be imparted to the scent emitting material by immersing, spraying or otherwise exposing said porous material to a solution containing the desired scent or fragrance. It should be made of a material that will impart the scent it holds to the surrounding air inside the packet 26. FIG. 3 is a side view of the scent dispensing packet showing how the space inside the packet is compressed when the outside walls of the packet are squeezed or activated. When that space is compressed, the air surrounding the scent emitting material is forced to escape to the outside environment 28 through the valve or opening in the packet wall. FIG. 4 is a side view of the scent dispensing packet showing what occurs when pressure on the walls of the packet is released. The walls of the packet start to return to their original shape. This in turn expands the volume of space inside the packet thus creating a vacuum inside the packet. Air flows back into the packet 30 through the airflow valve nozzle to fill the vacuum. FIG. 5 is a side view of the scent dispensing device after all of the air has returned to the inside of the packet to return the packet to an equalized air pressure state. FIG. 6 is a perspective front view of the packet before it has been fully assembled showing the location of the scent emitting material affixed to the inside of a bottom side of the packet 32. This scent dispensing packet can be manufactured by molding the packet in a flat, open position through a simple injection or stamp molding process. After the molding process and during assembly, the scent emitting material will be placed into the scent emitting material holder. This holder can also be molded into the design of the one piece packet. Then a top side of the packet 34 is folded at a flexible hinge 40 to meet the bottom side of the packet in the direction indicated 38. The hinge can be molded into the design of the one piece packet as well. Interlocking grooves 36 molded into three edges of the packet on both the top side and bottom side keep the packet closed after assembly.

Figure 7:
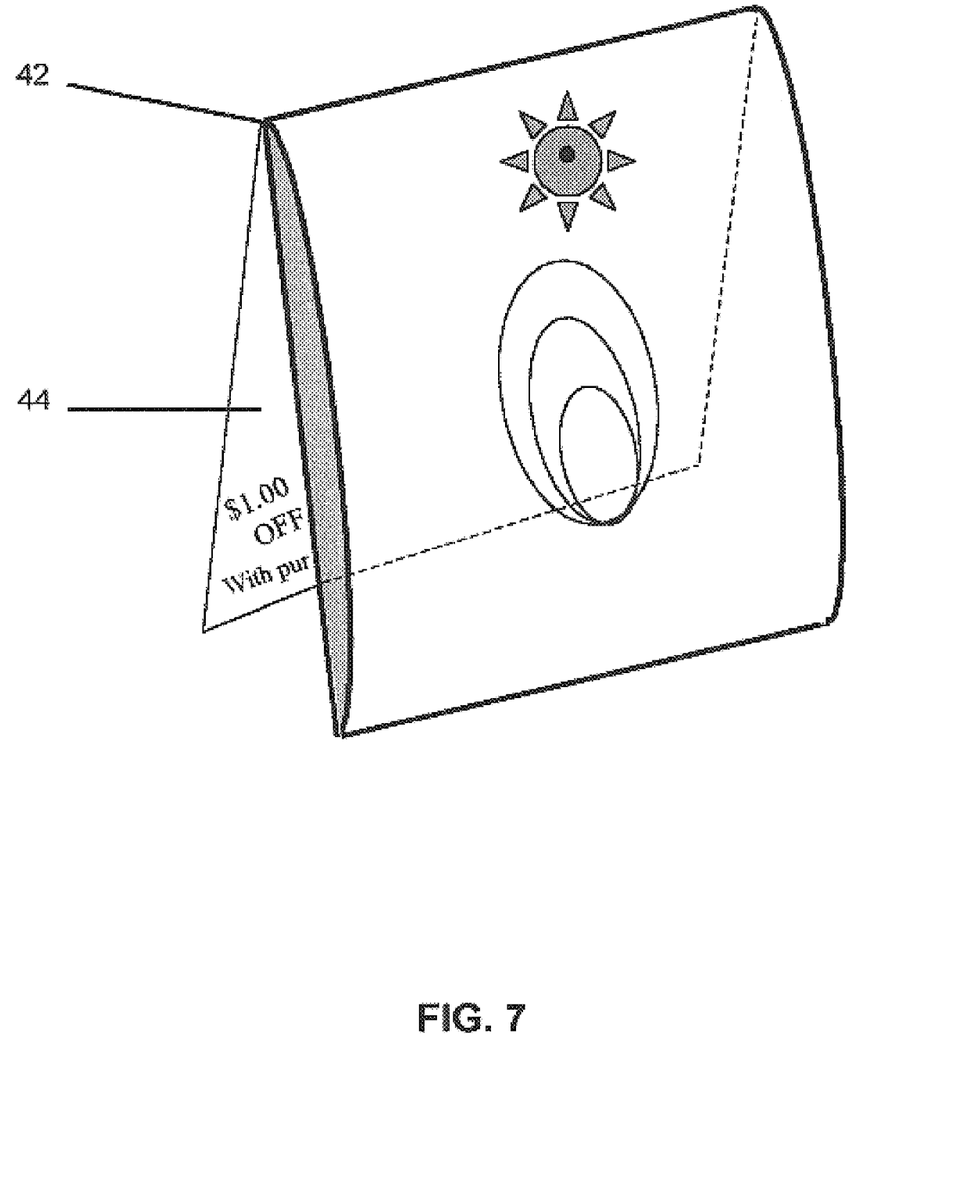
FIG. 7 is a perspective front view of the scent dispensing packet with a purchase incentive affixed.
Figure 8:
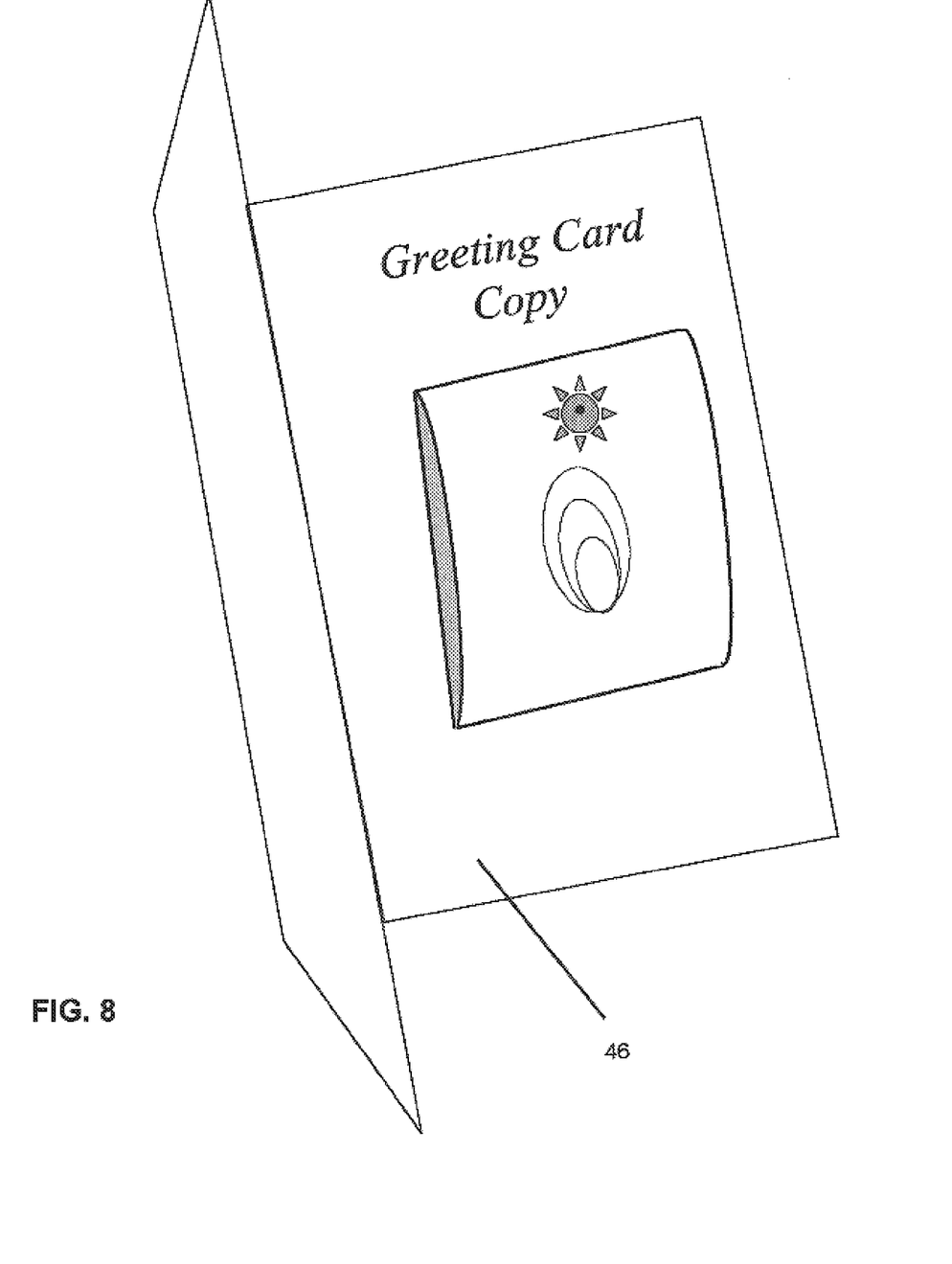
FIG. 8 is a perspective front view of the scent dispensing packet affixed to the inside page of a greeting card.
Figure 9:
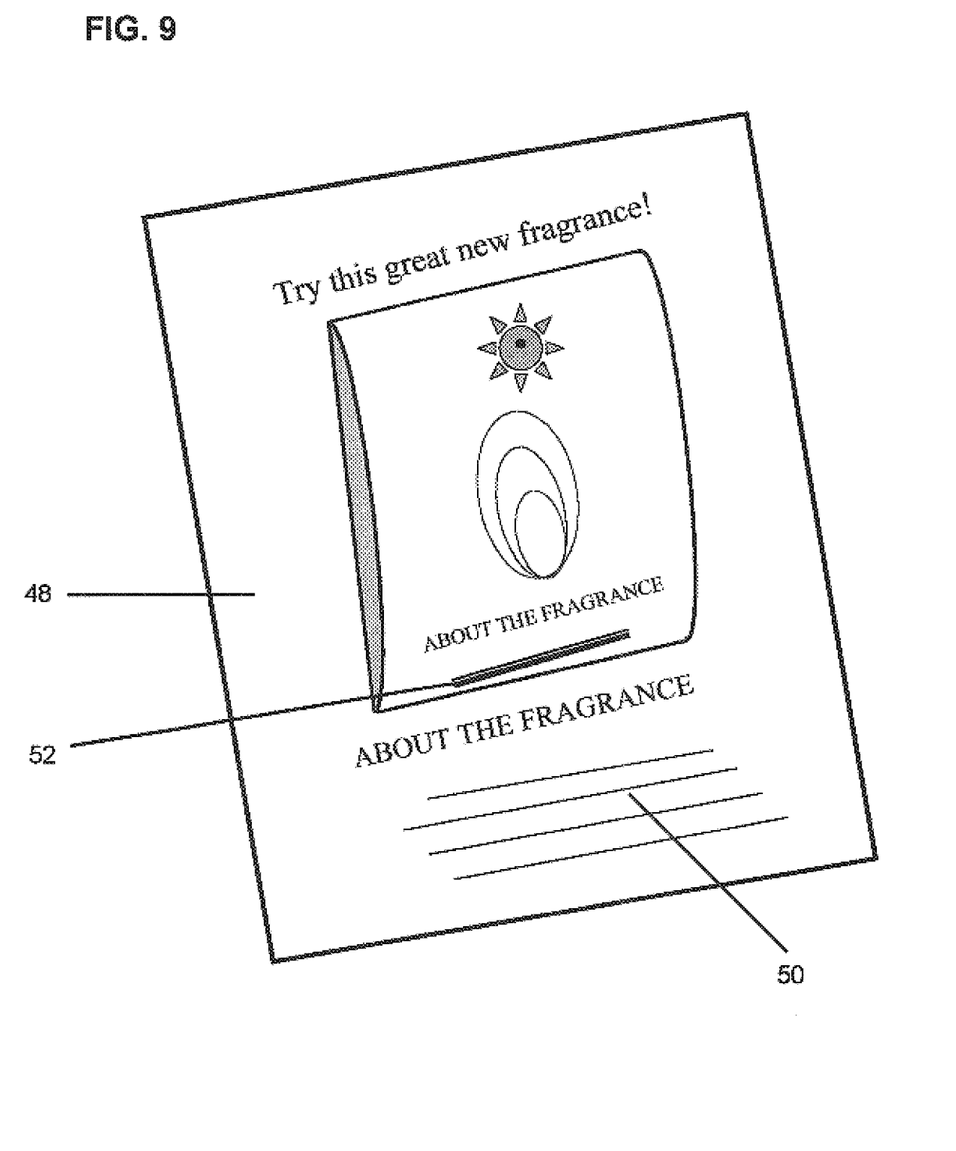
FIG. 9 is a perspective front view of the scent dispensing packet affixed to an advertising or promotion card.

Additional Embodiments—FIGS. 7–9

Additional embodiments are shown in FIGS. 7, 8, and 9 (perspective front view) FIG. 7 is a perspective front view of the scent dispensing packet with a purchase incentive 44 attached to the top of the packet 42. The incentive can be affixed with glue or other adhesive. FIG. 8 is a perspective front view of a greeting card showing the packet affixed to the inside of the card 46 similarly affixed with glue or other adhesive. FIG. 9 is a perspective front view of an advertising or promotion card 48 onto which the packet is affixed. A marketing copy can be included on the card 50 or directly on the packet 52.

What is claimed is:

1. A scent dispensing packet comprising:
   (a) a hollow cavity defined by outer resilient walls;
   (b) a porous and absorbent scent emitting material contained within and not defining any boundary of the cavity, the scent emitting material retaining a scent and causing the scent to be imparted to the air directly surrounding the scent emitting material; and
   (c) a valve in the outer resilient walls of the packet, the valve causing only air to escape from the packet only when pressure is applied to the outer walls of the packet, and allowing air to return to the inside of the packet once the pressure has been released, wherein:
      (1) the outer resilient walls protect the scent emitting material contained within the cavity from evaporation from direct exposure to the air external to the packet, allow the packet to be compressed when pressure is applied to the outer walls, and allow the packet to return to its original shape when the pressure is released; and
      (2) the packet is substantially flat and adapted to be provided within a greeting card.

2. The packet of claim 1, wherein the packet comprises an envelope shaped packet.

* * * * *